T 867021

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED OCTOBER 28, 1969

867 O.G. 1095

825,264
CANNULA COUPLER
Daniel E. Carter, 20 Ave. E, Rochester, N.Y. 14621
Filed May 16, 1969. Published Oct. 28, 1969
Int. Cl. A61m *5/00*
U.S. Cl. 128—214
9 Sheets Drawing. 14 Pages Specification

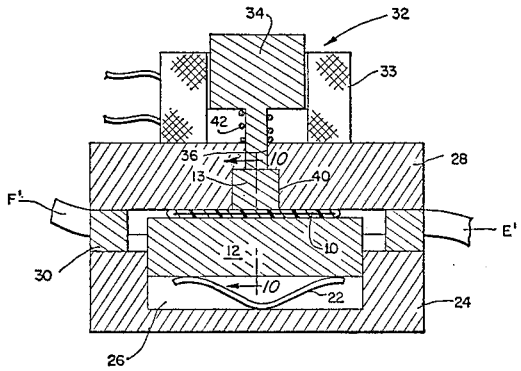

A cannula coupler for an artificial kidney machine comprises intersecting tubes and a valve which permits extracorporeal blood flow from the patient, through the machine, and back to the patient, and alternatively permits shunt flow which by-passes the machine. A fail-safe device actuates shunt flow in case the machine malfunctions.

Figure 1:
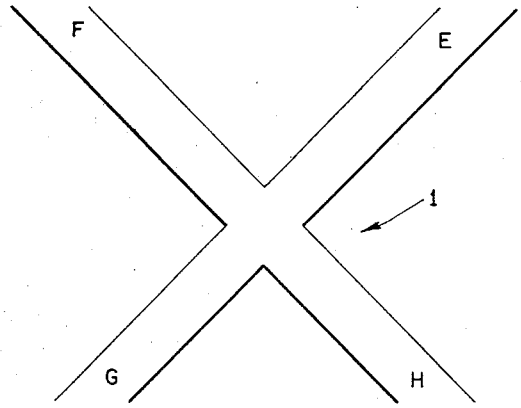
Figure 2:
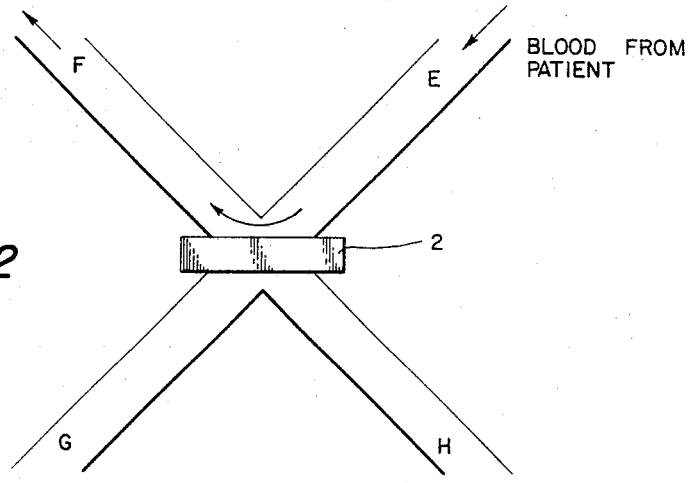
Figure 3:
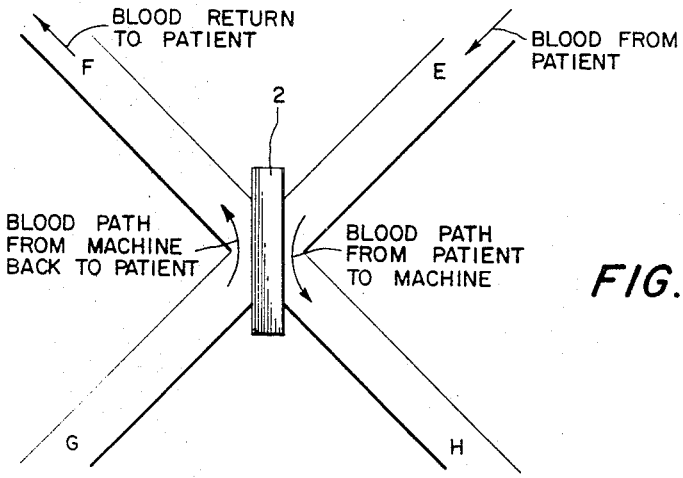
Figure 4:
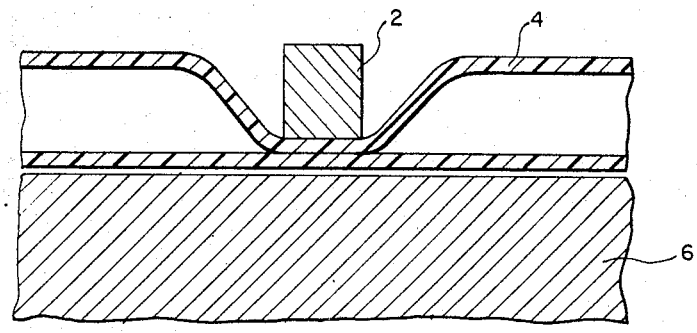
Figure 5:
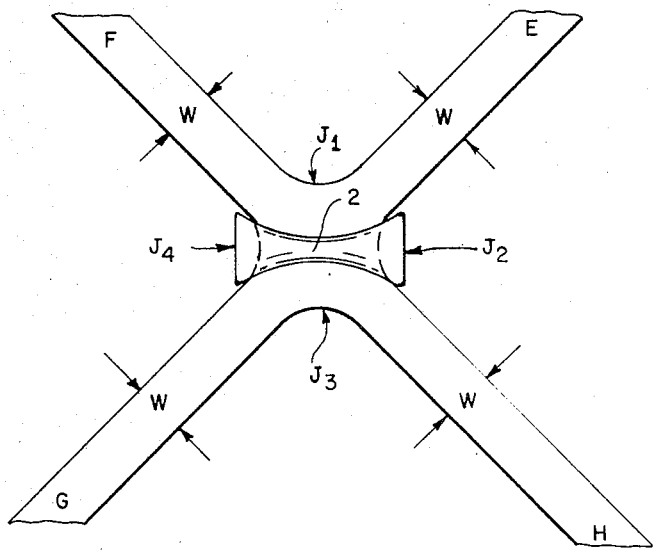
Figure 6:
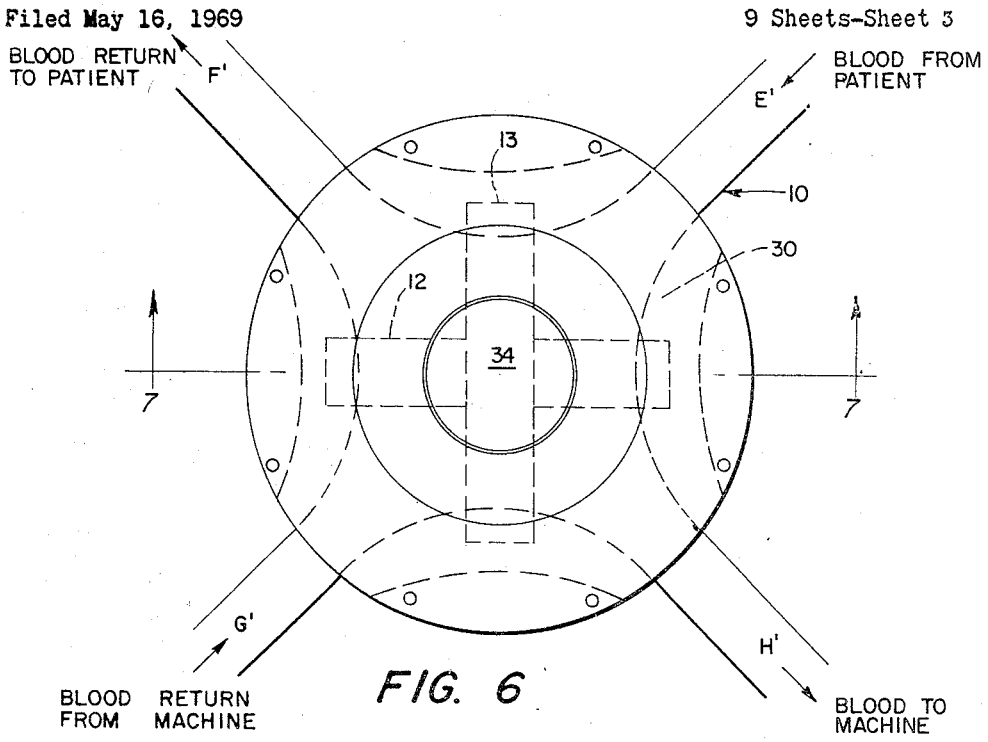
Figure 7:
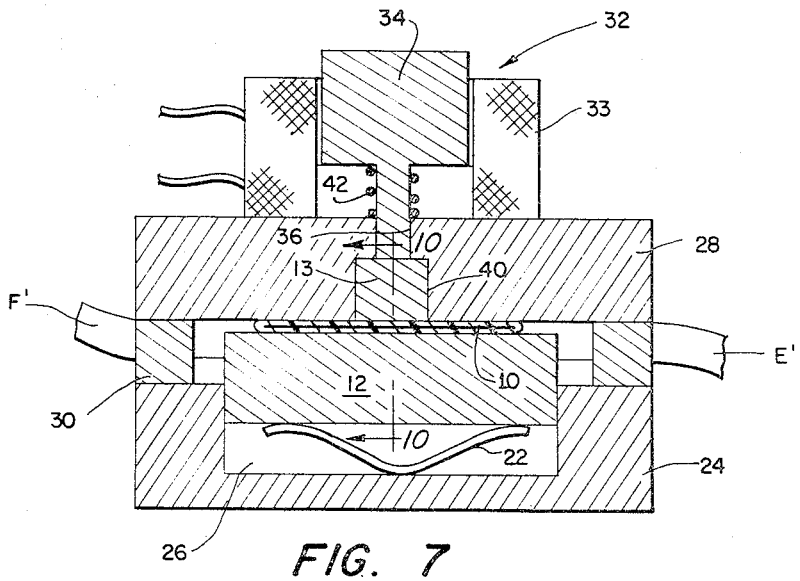
Figure 8:
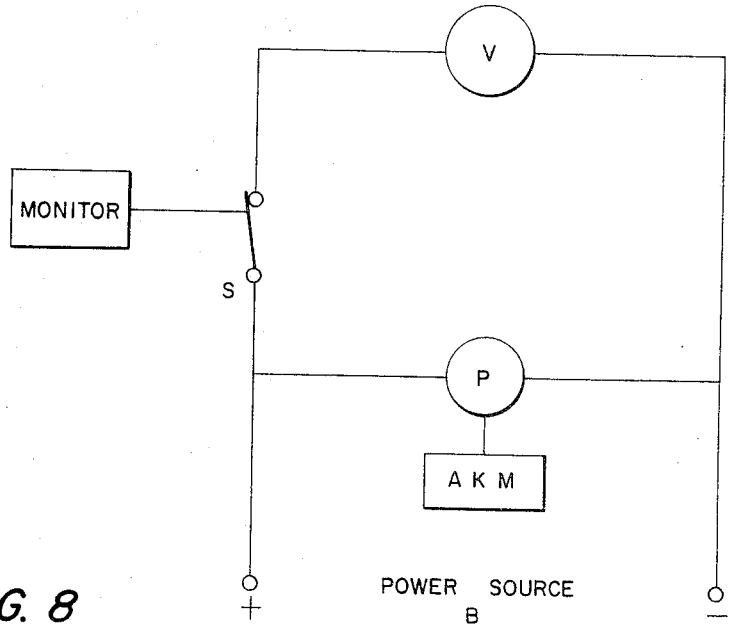
Figure 10:
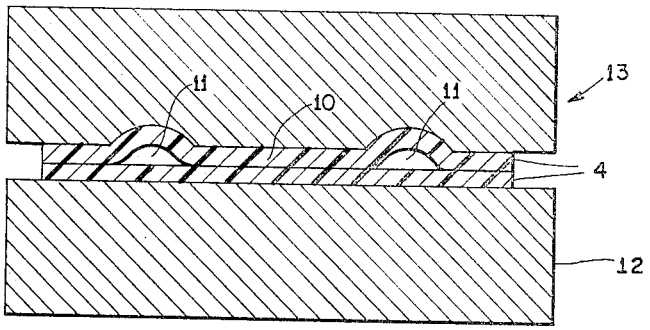
Figure 9:
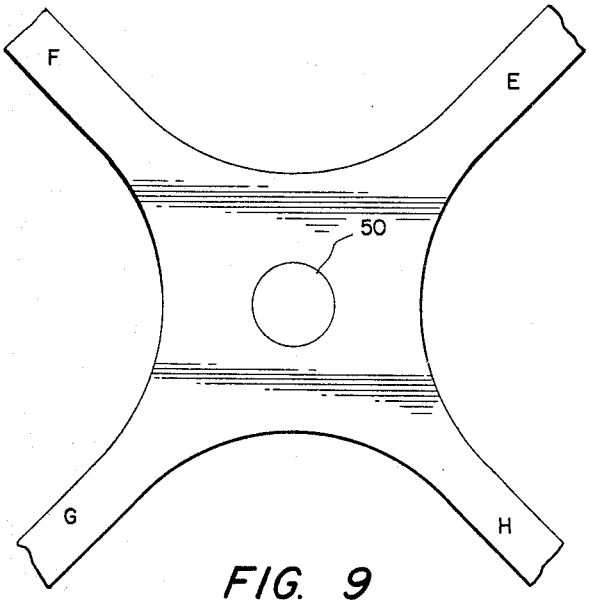
Figure 12:
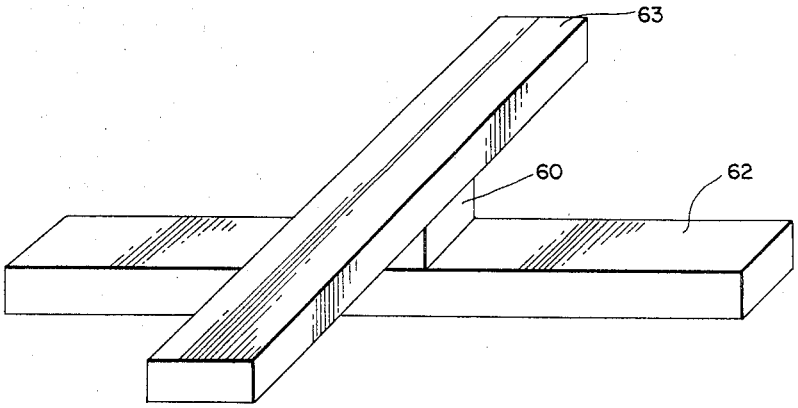
Figure 11:
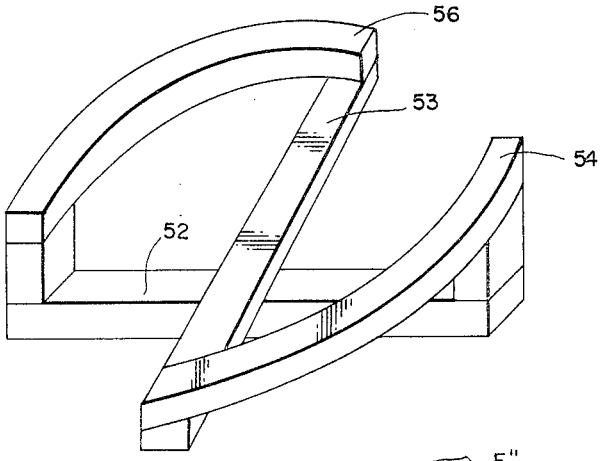
Figure 13:
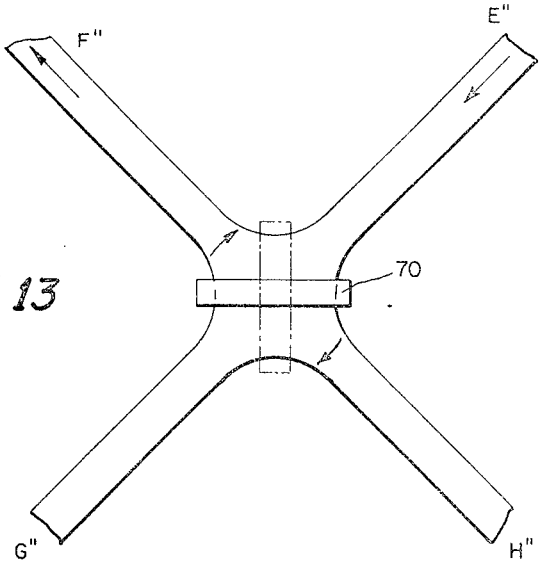
Figure 14:
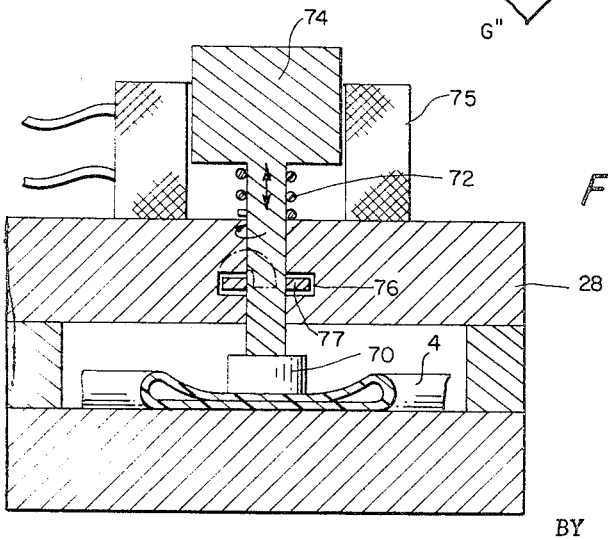
Figure 15:
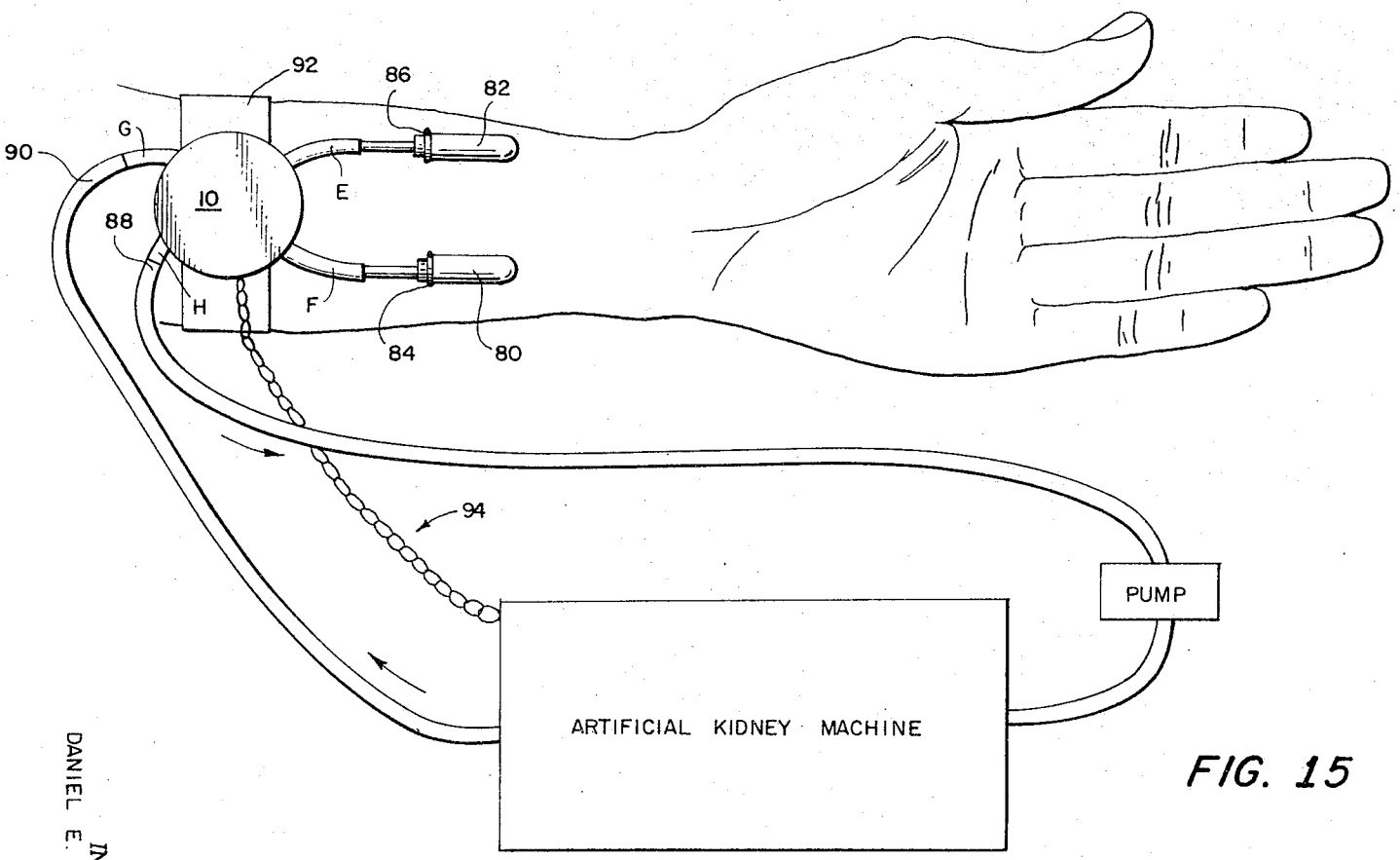
Figure 16:
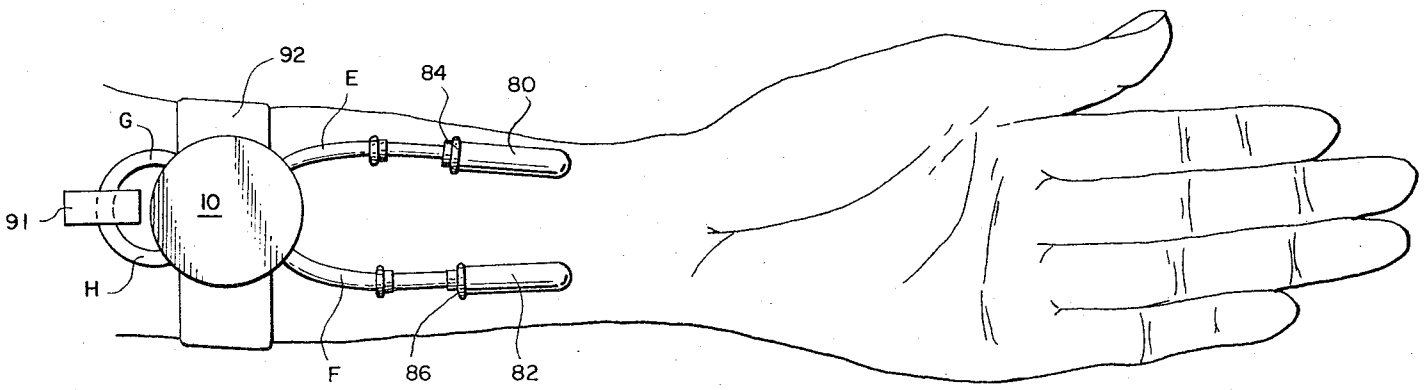
Figure 17:
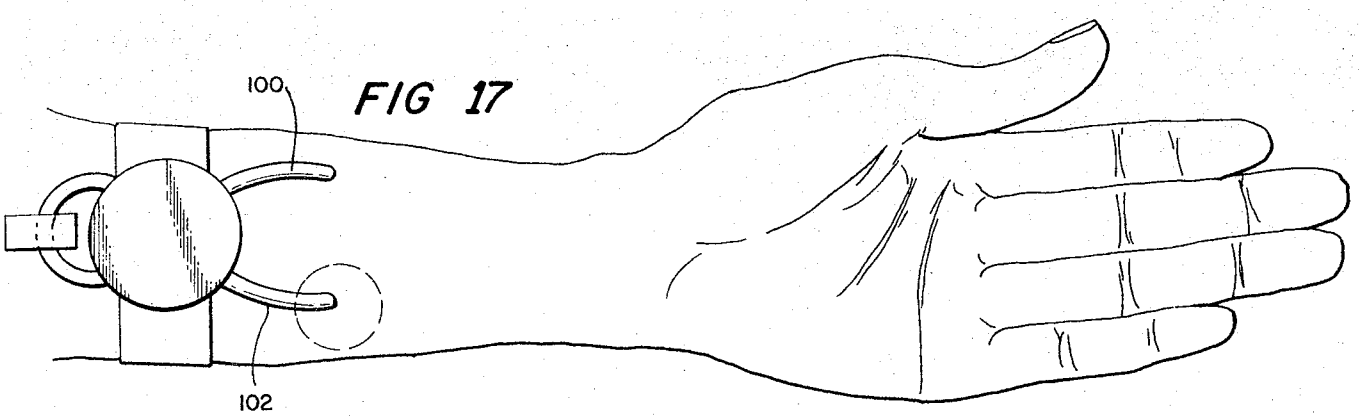
Figure 18:
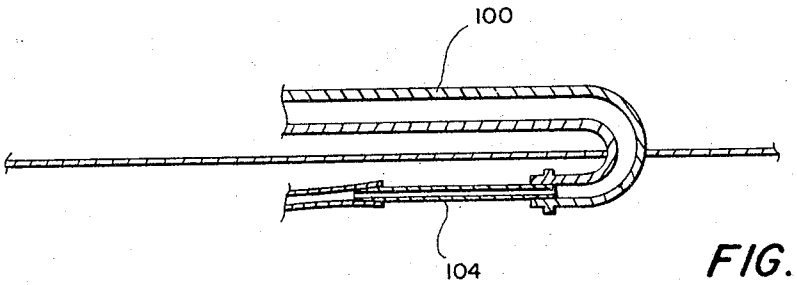

Referring to FIGS. 6 and 7, two bars 12 and 13 at 90° to one another are arranged on opposite sides of a hollow plastic coupler having four conduits extending therefrom. Bar 12 squeezes the coupler so that blood from the patient enters at E′ and is shunted to F′ and back to the patient.

When a linear solenoid 34 is energized, bar 13 presses the coupler and bar 12 down so that blood can flow from E′ to H′ and thence to an artificial kidney; then back through G′ and out at F′ to the patient.

A modification employs only one bar, with a rotary solenoid which raises, rotates, and lowers the bar. In others, two bars are connected together at 90° by a central member which extends through a central aperture in the hollow coupler; or by arcuate members.

825264 T867021

Oct. 28, 1969 D. E. CARTER DEF. PUB.

CANNULA COUPLER

Filed May 16, 1969 9 Sheets-Sheet 1

INVENTOR
DANIEL E. CARTER

BY WALTER O. HODSDON
HENRY M. CHAPIN
ATTORNEYS

T867021

825 264

Oct. 28, 1969 D. E. CARTER DEF. PUB.

CANNULA COUPLER

Filed May 16, 1969 9 Sheets-Sheet 2

INVENTOR
DANIEL E. CARTER

BY WALTER O. HODSDON
HENRY M. CHAPIN
ATTORNEYS

T867021

825264

Oct. 28, 1969 D. E. CARTER DEF. PUB.

CANNULA COUPLER

Filed May 16, 1969 9 Sheets-Sheet 3

INVENTOR
DANIEL E. CARTER

BY WALTER O. HODSDON
HENRY M CHAPIN
ATTORNEYS

T867021

825 264

DEF. PUB.

Oct. 28, 1969

D. E. CARTER

CANNULA COUPLER

Filed May 16, 1969

9 Sheets-Sheet 6

INVENTOR
DANIEL E. CARTER

BY WALTER O. HODSDON
HENRY M. CHAPIN
ATTORNEYS 825 264 T867021
DEF. PUB.

INVENTOR
DANIEL E. CARTER

BY WALTER O. HODSDON
HENRY M. CHAPIN
ATTORNEYS 825 264 T867021

Oct. 28, 1969 D. E. CARTER DEF. PUB.

CANNULA COUPLER

Filed May 16, 1969 9 Sheets-Sheet 6

INVENTOR
DANIEL E. CARTER

BY WALTER O. HODSDON
HENRY M. CHAPIN
ATTORNEYS

T867021

825 264

Oct. 28, 1969 D. E. CARTER DEF. PUB.

CANNULA COUPLER

Filed May 16, 1969 9 Sheets-Sheet 7

INVENTOR
DANIEL E. CARTER

BY WALTER O. HODSDON
HENRY M. CHAPIN
ATTORNEYS

T 867021

825 264
DEF. PUB.

Oct. 28, 1969

D. E. CARTER

CANNULA COUPLER

Filed May 16, 1969

9 Sheets-Sheet 8

INVENTOR
DANIEL E. CARTER

BY WALTER O HODSDON
HENRY M. CHAPIN
ATTORNEYS

INVENTOR
DANIEL E. CARTER

BY WALTER O. HODSDON
HENRY M. CHAPIN
ATTORNEYS